(12) United States Patent
Uflacker

(10) Patent No.: US 6,428,498 B2
(45) Date of Patent: Aug. 6, 2002

(54) SUCTION CATHETER FOR RAPIDLY DEBRIDING ABSCESSES

(76) Inventor: Renan Uflacker, 548 Overseer's Retreat, Mt. Pleasant, SC (US) 29464

( * ) Notice: Subject to any disclaimer, the term of this patent is extended or adjusted under 35 U.S.C. 154(b) by 0 days.

(21) Appl. No.: 09/291,452

(22) Filed: Apr. 14, 1999

Related U.S. Application Data

(60) Provisional application No. 60/081,678, filed on Apr. 14, 1998.

(51) Int. Cl.$^7$ ............................ A61B 17/20; A61B 17/32
(52) U.S. Cl. ........................... 604/22; 604/543; 606/171
(58) Field of Search .......................... 604/22, 523, 533, 604/539–544, 902, 27, 30, 35, 48; 606/167, 171–172, 170, 159

(56) References Cited

U.S. PATENT DOCUMENTS

| | | | |
|---|---|---|---|
| 3,890,970 A | * | 6/1975 | Gullen |
| 4,055,187 A | * | 10/1977 | Patel et al. |
| 4,513,745 A | * | 4/1985 | Amoils |
| 4,655,743 A | | 4/1987 | Hyde |
| 4,660,267 A | | 4/1987 | Wheeler |
| 5,106,364 A | * | 4/1992 | Hayafuji et al. |
| 5,248,297 A | * | 9/1993 | Takase |
| 5,290,303 A | | 3/1994 | Pingleton et al. |
| 5,295,980 A | | 3/1994 | Ersek |
| 5,527,332 A | * | 6/1996 | Clement |
| 5,780,849 A | * | 7/1998 | Miller ........................ 606/159 |
| 5,928,218 A | * | 7/1999 | Gelbfish |
| 5,941,845 A | * | 8/1999 | Tu et al. ...................... 604/53 |

* cited by examiner

Primary Examiner—Brian L. Casler
Assistant Examiner—Lohn H. Thanh
(74) Attorney, Agent, or Firm—Hodgson Russ LLP

(57) ABSTRACT

A medical device 10 particularly adapted for debriding an abscess, phlegmon, or hematoma in a human or veterinary patient, for removing debrided and other materials from the abscess and for draining the abscess first includes a flexible catheter 12 having a longitudinally extending flow lumen 14, a rounded distal tip 16, a side portion 18 extending proximally from the distal tip 16 and an oval or other lateral opening 20, 44 or 46 extending through the side portion 18. The device also includes a cutting cannula 22 positionable in and longitudinally slidable in the flow lumen 14 in the catheter 12. The cannula 22 has an open distal end 24 and a sharp, beveled circumferential cutting edge 26 formed on the open distal end 24, the circumferential cutting edge 26 being disposed perpendicularly to the flow lumen 14 of the catheter 12. Upon movement of the cannula 22 in the flow lumen 14, the cutting edge 26 moves across the lateral opening 20 and cuts any material extending through the lateral opening 20 of the catheter 12. The cannula 22 further has a proximal end 30 opposite the open distal end 24 adapted for the application of suction thereto. The catheter 12 is capable of draining the abscess even when the cutting cannula 22 is not positioned in the flow lumen 14. The device 10 can also include a side arm 40 connected to the proximal end 36 of the catheter 12 in fluid communication with the flow lumen 14 of the catheter 12, and a fitting 42 connecting the side arm 40 to the proximal end 36 of the catheter 12. The fitting 42 can contain a seal element 38 through which the cannula 22 can be passed.

18 Claims, 3 Drawing Sheets

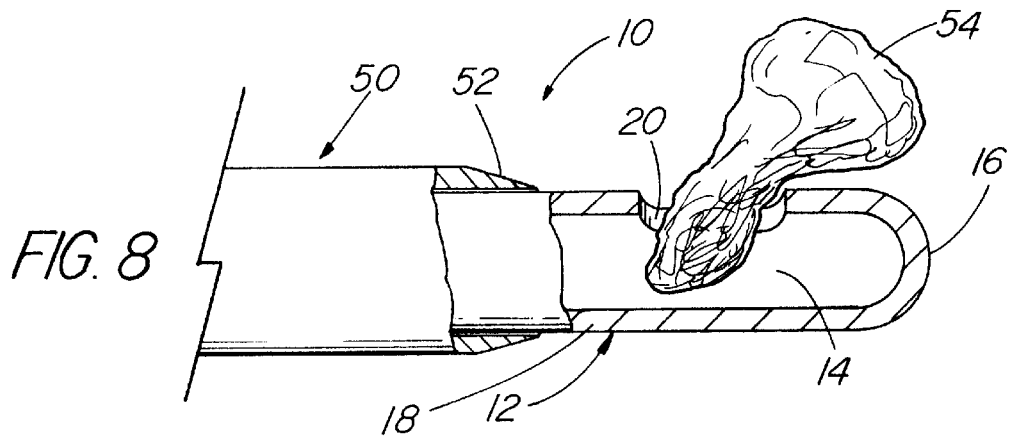
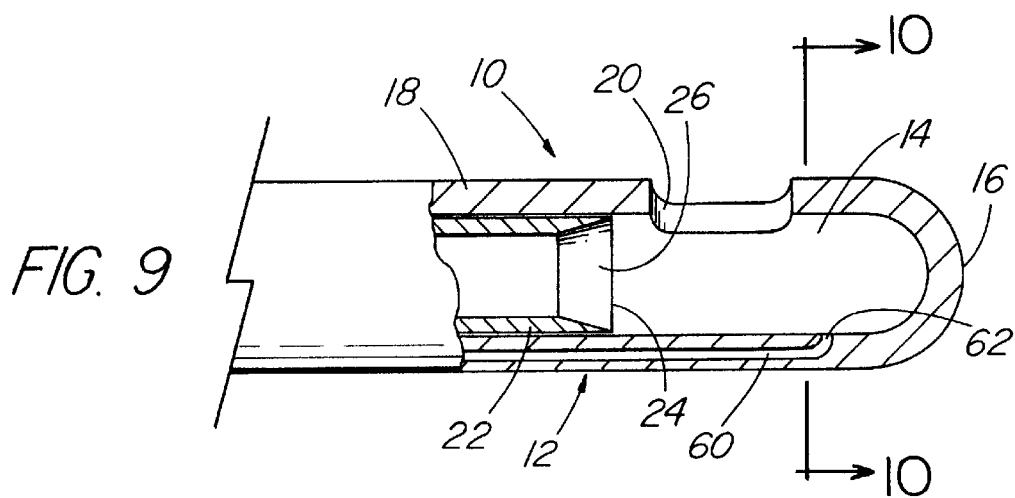
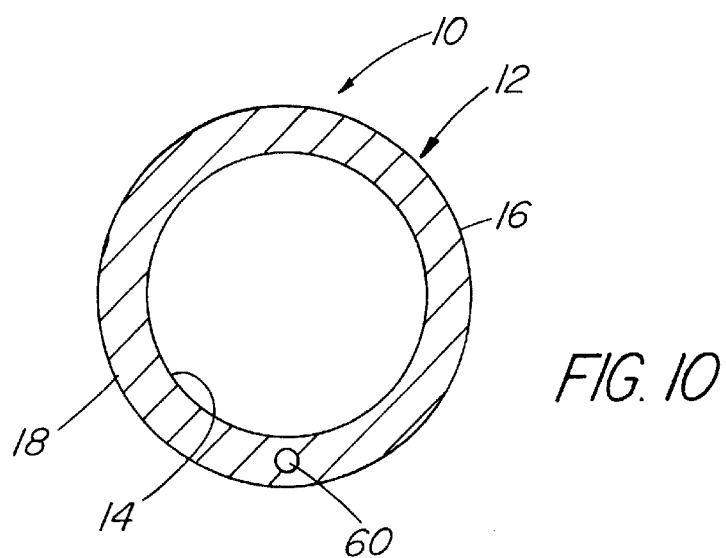

SUCTION CATHETER FOR RAPIDLY DEBRIDING ABSCESSES

CROSS REFERENCE TO RELATED APPLICATIONS

This application claims priority of provisional application Ser. No. 60/081,678, filed Apr. 14, 1998.

TECHNICAL FIELD

This invention relates generally to medical devices, and more particularly to a device for debriding, aspirating, and draining an abscess present in a human or veterinary patient.

BACKGROUND OF THE INVENTION

A variety of locations within the body of a human or veterinary patient are subject to developing an abscess after the occurrence of infection or contamination at such locations. Contamination can result from structural changes or damage to tissues in the body caused by injury or surgery, or can result from structural irregularities arising naturally within the body. Abscesses often develop in an existing tract or passage within the body, such as in mucus glands, for example, rectal mucus glands. An abscess can perhaps most simply be considered as a sac containing bacteria, body fluids and sera, blood clots, dead or necrotic tissue, and the like. Treatment of an abscess entails debriding the abscess and draining it of such materials contained in it.

A variety of suction and other devices are known for cutting and removing a wide range of materials from the body at locations other than abscesses. Such devices usually possess a structure which is particularly adapted to the location of interest, and which is particularly adapted to the material to be removed. Unfortunately, such devices are ill-suited to the particular problems encountered when draining and debriding abscesses. More particularly, such devices are generally rigid and are therefore not suited for introduction into and through an existing tract or passage in which an abscess has formed.

For example, U.S. Pat. No. 4,660,267 (C. R. Wheeler, Apr. 28, 1987) discloses a method of fabricating a surgical probe for performing arthroscopic surgery. The probe resulting from the method includes an outer tube and an inner tube which rotates at relatively high speeds within the outer tube. A bearing is formed by an inwardly extending bearing surface on the distal end of the outer tube and a complementary bearing surface on the distal end of the inner tube. Each of the outer and inner tubes has aligned openings on one side near their distal ends, such that the high speed rotation of the inner tube within the outer tube shaves tissue entering the side openings. Suction is applied to the inner tube to draw the shaved tissue away from the distal end of the probe to avoid clogging of the openings. The bearing provides both radial and longitudinal thrust bearing support to the device during rotation of the inner tube.

U.S. Pat. No. 5,295,980 (R. A. Ersek, Mar. 22, 1994) is directed to an infusion and aspiration catheter useful, for example, during liposuction or a biopsy, which includes a cannula member having a rounded, partially open, blunt insertion tip, and a stilette (sic., presumably a stylet) which is received in the cannula member. The stilette can be rotated or moved longitudinally in the cannula member to cut, saw or grasp a tissue specimen. The patent notes at column 5, lines 5 through 10, that it is important that the opening of the cannula member be located on a taper between the blunt end of the member and the cylindrical shaft portion of the member, but that the opening encompass neither the distal end nor any portion of the shaft of the member.

U.S. Pat. No. 5,290,303 (E. D. Pingleton, Mar. 1, 1994) discloses a surgical cutting instrument for laparoscopic or endoscopic use which includes an inner rotary tube member having a cutting edge at its distal end which extends from a stationary sheath which prevents tissue from wrapping around the rotary tube member. The inner cutting member tube includes a hollow passageway for suctioning and aspirating tissue and fluid, and the instrument further includes an outer safety shield having a rounded distal end for preventing puncture of a surgical tissue bag, or for preventing the unintentional cutting of tissue. An access channel for accepting tissue is located laterally about the distal end of the safety tube, and acts as a jaw which feeds tissue into a rotary cutting edge extending circumferentially about the distal end of the inner member.

Finally, U.S. Pat. No. 4,655,743 (L. L. Hyde, Apr. 7, 1987) is directed to an irrigation-aspiration device useful in eye surgery and which includes an outer cannula and an inner cannula which can be reciprocated within the outer cannula. Tissue is drawn into the device through a lateral suction port located proximal to the distal tip of the inner cannula, and is cut between the suction port and the distal tip of the outer cannula. The inner cannula is bent along its length and is springy so that the port abrades against the end of the outer cannula with a biting or cutting action. An inner lumen of the inner cannula is connected to vacuum or a suction source to draw fragments of the eye into the port for cutting.

While these devices appear to be useful for their individual and particularly intended purposes, it would appear that none of these devices is particularly adapted for debriding and draining an abscess, phlegmon, or hematoma, and that none of these devices is capable of performing not only their individual and particularly intended purposes, but also the additional functions of a conventional drainage catheter. In particular, substantially all of these devices include a rigid first cutting cannula inside a rigid second cutting cannula. Such devices are not intended to be left in a patient to allow drainage of a site of interest, for example, an abscess, after performing one surgical technique or another.

It would be highly desirable to have a debriding device which was particularly adapted for debriding and draining an abscess or phlegmon in a human or veterinary patient, and which was structured to meet the particular problems encountered in debriding and draining an abscess. It would also be highly advantageous to have such a device which was sufficiently flexible to allow it to be introduced into and through any existing tract in which an abscess has developed. It would further be advantageous to have such a device in which it is primarily the cutting cannula which shears any tissue or other material to be debrided, in contrast to the more rigid prior devices in which the stiffness of an outer cannula contributes substantially to the shearing of such tissue or other material. It would be still further advantageous to have such a device which was capable of cutting blood clots and dead or necrotic tissues in or adjacent to the abscess, and which was capable of removing, by suction, any materials so cut. Finally, it would also be highly desirable to have such a device which could be left in a patient for some time after the performance of a surgical technique, for draining the site at which the technique was performed.

SUMMARY OF THE INVENTION

The foregoing problems are solved and a technical advance is achieved in an illustrative medical device particularly adapted for debriding and draining abscesses present in a human or veterinary patient. The device of the present invention is directed to a specific combination which either comprises or consists of a catheter having a lateral opening, and a cutting needle or cannula (hereinafter, "cutting cannula") received in the catheter and having a circumferential cutting edge which can be slid along the lateral opening of the catheter. Longitudinal movement of the cutting cannula in the catheter causes the circumferential cutting edge to sever any material which extends through the lateral opening. Suction is applied to the proximal end of the cutting cannula to draw material from the abscess through the lateral opening of the catheter, through the cutting cannula and out of the device. The catheter is preferably flexible and is adapted to allow drainage of the abscess even when the cutting cannula is not positioned in the catheter.

This specific cutting structure is quite different from the prior devices mentioned above, which have been employed for decidedly different purposes. First, the prior devices mentioned above generally include a first rigid cutting cannula inside a second rigid cutting cannula. The present invention, in contrast, includes a catheter as its outer member. The use of the catheter in the present invention allows the device of the present invention to not only debulk the abscess, but also to remain in position and drain the abscess after debriding has been carried out with the present device. Second, the circumferential cutting edge on the cutting cannula makes the cutting cannula a front-cutting needle, rather than a side-cutting needle as is employed in many of the prior devices mentioned above. Because of this, the tissue to be debrided is sheared mainly by the cutting cannula itself; the lateral opening (in conjunction with any applied suction) merely holds the tissue in place, rather than actively contributing to shearing of the tissue. The first of these differences, that is, the use of a catheter in the device instead of a rigid cannula, is probably the more important with regard to the good utility enjoyed by the present invention.

In a first aspect, then, the present invention is directed to a medical device particularly adapted for debriding an abscess in a human or veterinary patient, for removing debrided and other materials from the abscess and for draining the abscess, comprising: a catheter having a longitudinally extending flow lumen defined therein, a distal tip closing the flow lumen, a side portion extending proximally from the distal tip and a lateral opening formed in and extending through the side portion; and a cutting cannula positionable in and longitudinally slidable in the flow lumen in the catheter, having an open distal end and a circumferential cutting edge formed on the open distal end, the circumferential cutting edge moving across the lateral opening of the catheter upon longitudinal sliding movement of the cutting cannula in the flow lumen of the catheter and thereby cutting any material extending from the abscess and through the lateral opening of the catheter.

Preferably, the circumferential cutting edge of the cutting cannula is sharp and beveled from the outer surface to inner surface. Alternatively, the cutting edge can be beveled from the inner to the outer surface (countersunk). The circumferential cutting edge of the cutting cannula is disposed perpendicularly to the flow lumen of the catheter. The cutting cannula is preferably composed of a stainless steel circumferentially ground needle cannula, although tetrafluoroethylene, polyethylene terephthalate, or any other suitable medical grade material can be used.

The distal tip of the catheter is preferably rounded, and the lateral opening of the catheter can be oval in shape or otherwise shaped as convenient. The lateral opening can extend about one third of the way around the catheter and about 5 to 6 mm along the direction of the flow lumen. The catheter is adapted for introduction to the abscess and drainage of the abscess even when the cutting cannula is not positioned in the flow lumen of the catheter. The catheter is preferably about 10–16 French (3–5 mm) in diameter and about 33 cm long, and can be composed of vinyl non-radiopaque tubing, a urethane tubing such as USI Petrothane, or another appropriate flexible medical grade material.

The debriding device of the present invention preferably further comprises a suction source connectable to the proximal end of the cutting cannula for withdrawing any materials cut by the circumferential cutting edge of the cutting cannula, as well as any other materials contained in the abscess, phlegmon, or hematoma. The device preferably further comprises a seal element located adjacent to the proximal end of the catheter, through which the cutting cannula can be passed. The device can still further comprise a side arm in fluid communication with the flow lumen of the catheter, connected to the proximal end of the catheter by a fitting containing the seal element.

In a second aspect, the present invention is directed to a medical device particularly adapted for debriding an abscess in a human or veterinary patient, for removing debrided and other materials from the abscess and for draining the abscess, comprising: a flexible catheter having a longitudinally extending flow lumen defined therein, a rounded distal tip closing the flow lumen, a side portion extending proximally from the distal tip and an oval lateral opening formed in and extending through the side portion; and a cutting cannula positionable in and longitudinally slidable in the flow lumen in the catheter, having an open distal end and a sharp, beveled circumferential cutting edge formed on the open distal end, the circumferential cutting edge being disposed perpendicularly to the flow lumen of the catheter and moving across the oval lateral opening of the catheter upon longitudinal sliding movement of the cutting cannula in the flow lumen of the catheter and thereby cutting any material extending from the abscess and through the lateral opening of the catheter; wherein the cutting cannula further has a proximal end opposite the open distal end adapted for the application of suction thereto; wherein the catheter is adapted for introduction to the abscess and drainage of the abscess when the cutting cannula is not positioned in the flow lumen of the catheter; wherein the catheter is about 10–16 French (3–5 mm) in diameter and is about 33 cm long; wherein the catheter further has a proximal end opposite the distal tip, and wherein the device further comprises a seal element located adjacent to the proximal end of the catheter through which the cutting cannula can be passed; wherein the lateral opening of the catheter extends about one third of the way around the catheter and extends about 5 to 6 mm along the direction of the flow lumen; and wherein the device further comprises a side arm connected to the proximal end of the catheter in fluid communication with the flow lumen of the catheter and a fitting connecting the side arm to the proximal end of the catheter, the seal element being contained in the fitting.

In a final aspect, the present invention is directed to a medical device particularly adapted for debriding an abscess, phlegmon, or hematoma in a human or veterinary patient, for removing debrided and other materials from the abscess and for draining the abscess, consisting of: a flexible catheter having a longitudinally extending flow lumen defined therein, a rounded distal tip closing the flow lumen, a side portion extending proximally from the distal tip and an oval lateral opening formed in and extending through the side portion; and a cutting cannula positionable in and longitudinally slidable in the flow lumen in the catheter, having an open distal end and a sharp, beveled circumferential cutting edge formed on the open distal end, the circumferential cutting edge being disposed perpendicularly to the flow lumen of the catheter and moving across the oval lateral opening of the catheter upon longitudinal sliding movement of the cutting cannula in the flow lumen of the catheter and thereby cutting any material extending from the abscess and through the lateral opening of the catheter; wherein the cutting cannula further has a proximal end opposite the open distal end adapted for the application of suction thereto; wherein the catheter is adapted for introduction to the abscess and drainage of the abscess when the cutting cannula is not positioned in the flow lumen of the catheter; wherein the catheter is about 10–16 French (3–5 mm) in diameter and is about 33 cm long; wherein the catheter further has a proximal end opposite the distal tip, and wherein the device further consists of a seal element located adjacent to the proximal end of the catheter through which the cutting cannula can be passed; wherein the lateral opening of the catheter extends about one third of the way around the catheter and extends about 5 to 6 mm along the direction of the flow lumen; and wherein the device further consists of a side arm connected to the proximal end of the catheter in fluid communication with the flow lumen of the catheter and a fitting connecting the side arm to the proximal end of the catheter, the seal element being contained in the fitting.

The abscess debriding device of the present invention possesses several significant advantages. It is capable of cutting blood clots and dead or necrotic tissues in or adjacent to the abscess and is capable of removing, by suction applied to the cutting cannula, any materials so cut. The catheter of the device is sufficiently flexible to allow the device to be introduced into and through a tract in which an abscess has developed. The catheter of the device is also sufficiently flexible to further allow the device to be left in a patient for some time after the performance of a surgical technique, for draining the site at which the technique was performed. The abscess drainage device of the present invention is particularly adapted for all of these tasks, not just debriding as is the case with prior devices, and is structured to meet the particular problems encountered during debriding and draining an abscess, phlegmon, or hematoma. Advantageously, in the device of the present invention it is primarily the cutting cannula which shears the tissue or other material to be debrided, in contrast to the more rigid prior devices in which the stiffness of an outer cannula contributes substantially to the shearing of such tissue or other material.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 8 is a partially sectioned side view of a portion of another preferred embodiment of the present invention;

FIG. 9 is a partially sectioned side view of a portion of yet another preferred embodiment of the present invention; and FIG. 10 is an enlarged cross-sectional view of the catheter of FIG. 9 taken along the line 10—10.

DETAILED DESCRIPTION

Figure 1:
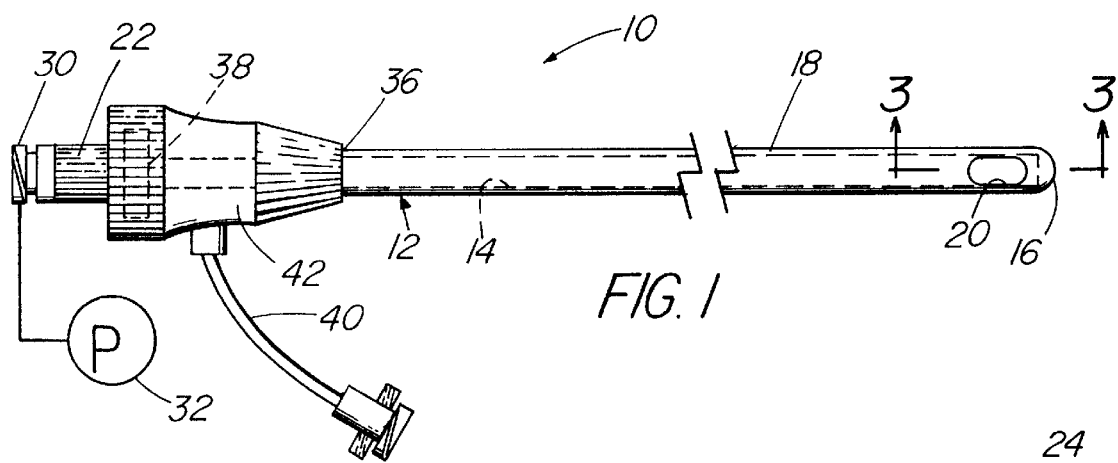
FIG. 1 is a side view of the preferred embodiment of the present invention.
Figure 4:
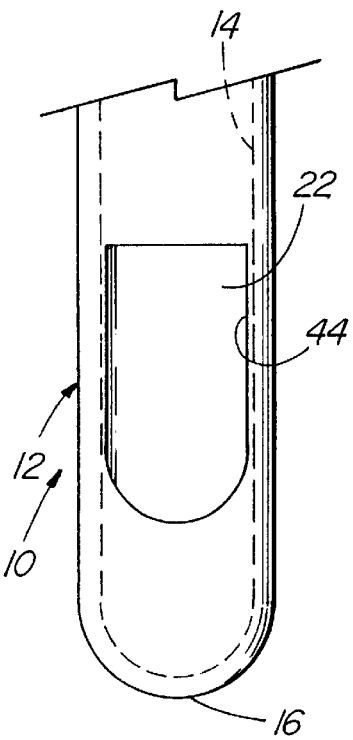
FIGS. 4 and 5 are side views of portions of other preferred embodiments of the present invention.
Figure 5:
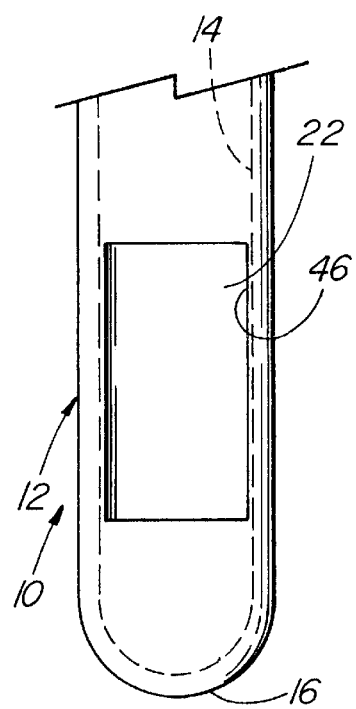

With reference first to FIG. 1, a medical device 10 according to the present invention for debriding an abscess in a human or veterinary patient, for removing debrided and other materials from the abscess and for draining the abscess, is thereshown. As used herein, "debriding" can include aspirating, suctioning, debulking, and/or draining. The medical device 10 first comprises or consists of a drainage catheter 12 of generally circular cross-section, composed of a flexible medical grade material, such as a flexible medical grade material, vinyl, vinyl non-radiopaque tubing, polyethylene, a soft polymer material, a urethane tubing such as USI Petrothane, or the like. The catheter 12 is, by itself, adapted for introduction to the abscess and drainage of the abscess. Introduction may of course be assisted by an additional outer introducer sheath (not shown) such as a peel-away sheath. The catheter 12 has a longitudinally extending flow lumen 14 formed therein, and a rounded distal tip 16 closing the flow lumen 14. The catheter 12 also includes a generally cylindrical side portion 18 extending proximally of the distal tip 16. Drainage of the abscess is provided via an oval lateral opening 20 formed in and extending through the side portion 18 of the catheter 12. Alternative shapes for the lateral opening, such as a D-shaped lateral opening 44 or a rectangular lateral opening 46 are shown in FIGS. 4 and 5, respectively.

The dimensions of the catheter 12 and its lateral opening 20 (or 44 or 46) are chosen as convenient for the location and dimensions of the abscess to be debrided and drained. An exemplary catheter 12 can be about 10–16 French (3–5 mm) in outer diameter and about 33 cm long. The lateral opening 20, 44 or 46 of the catheter 12 can extend about one third of the way around the circumference of the catheter 12, and can extend about 5 to 6 mm along the catheter 12 in the direction of the flow lumen 14. Of course, a wide variety of other dimensions and proportions can be selected to adapt the medical device 10 of the present invention to the site of the particular abscess to be debrided and drained.

Figure 6:
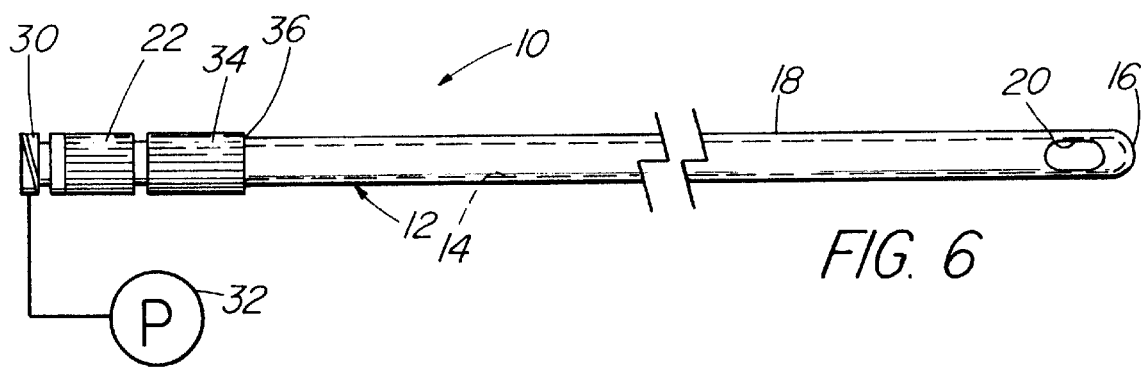
FIG. 6 is a side view of another preferred embodiment of catheter of FIG. 1.

Conveniently, the catheter 12 further has a proximal end 36 located opposite the distal tip 16. The medical device 10 of the present invention can conveniently comprise a side arm 40 disposed in fluid communication with the flow lumen 14 of the catheter 12. The side arm 40 is connected to the proximal end 36 of the catheter 12 by a fitting 42 of any convenient shape. The fitting 42 can, for example, be a large body CHECK-FLO™ fitting (product of Cook, Incorporated, Bloomington, Ind. or the like. The side arm 40 provides for drainage of the abscess via the catheter 12 in the conventional fashion after the abscess has been debrided by the medical device 10 of the present invention. The catheter 12 can be left in place for such drainage over short or long term. Drainage can be assisted by the application of suction (not shown) to the side arm 40 opposite its attachment to the fitting 42 in a conventional manner. The medical device 10 can further comprise penetrable, self-healing seal element 38 (shown only in phantom) located adjacent to the proximal end 36 of the catheter 12, for example, contained in the fitting 42, to allow suction through the catheter 12 and side arm 40. In another preferred embodiment, the fitting 42 including the side arm 40 and self-healing element 38 can be replaced by a standard hub 34 with a luer fitting without a means to seal a coaxial inner member as depicted in FIG. 6.

Figure 2:
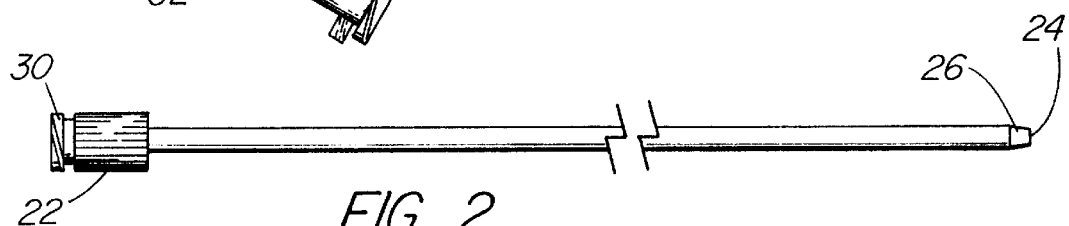
FIG. 2 is a side view of a portion of the preferred embodiment of the present invention.
Figure 3:
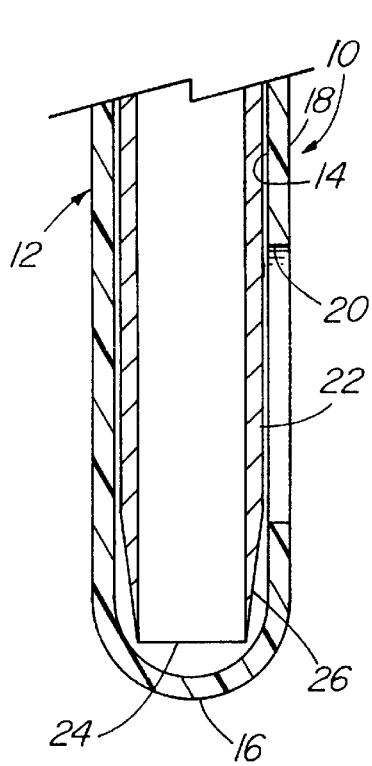
FIG. 3 is a cross-sectional view taken along line 3—3 of FIG. 1.
Figure 7:
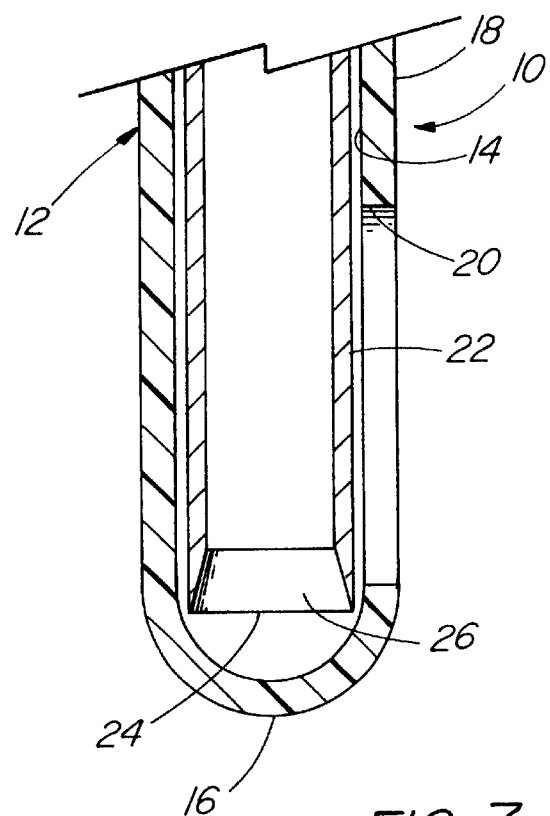
FIG. 7. is a side view of a portion of another preferred embodiment of the cutting cannula of FIG. 2

With continued reference to FIG. 1, but with further reference to FIGS. 2 and 3, the medical device 10 of the present invention also comprises or consists of a cutting needle or cannula 22 (hereinafter, "cutting cannula") positionable in and longitudinally slidable in the flow lumen 14 of the catheter 12 for cutting, severing and/or morcelating any material (such as blood clots, dead or necrotic tissue or the like) present in or at the abscess, which extends from the abscess and through the lateral opening 20, 44 or 46 of the catheter 12. The cutting cannula 22 has an open distal end 24 and a sharp, beveled circumferential cutting edge 26 formed on the open distal end 24. The bevel of distal end 24 can be formed from either the outer to the inner surface as in FIG. 1, or from the inner to the outer surface (countersunk) as in the other preferred embodiment depicted in FIG. 7. The circumferential cutting edge 26 of the cutting cannula 22 is preferably disposed perpendicularly to the flow lumen 14 of the catheter 12.

The cutting cannula 22 is introduced into the flow lumen 14 of the catheter 12 through the seal element 38 in the fitting 42. Upon longitudinal sliding movement of the cutting cannula 22 in the flow lumen 14 of the catheter 12, the circumferential cutting edge 26 of the cutting cannula 22 moves across the lateral opening 20, 44 or 46 of the catheter 12 to cut the material to be debrided. The cutting cannula 22 further has a proximal end 30 opposite the open distal end 24, and the medical device 10 preferably further comprises a suction source 32 (such as a vacuum pump or the like) connectable to the proximal end 30 of the cutting cannula 22. The seal element 38 assists aspiration of the abscess by preventing the undesirable flow of air through the flow lumen 14 of the catheter 12 and directly through the cutting cannula 22. Furthermore, the catheter 12 can be connected directly to the suction source 22 without the inner cutting cannula 22 present for purposes of further aspiration and drainage of material and fluids from the abscess site.

The cutting cannula 22 can be composed of any suitable medical grade material that maintains its shape sufficiently to allow the circumferential cutting edge 26 to remain sharp enough to cut the material to be debrided. The preferred material is a stainless steel circumferentially ground needle cannula, although tetrafluoroethylene, polyethylene terephthalate, or any other suitable medical grade material can be used. Like the catheter 12, the cutting cannula 22 is preferably of generally circular cross-section, and has an outside diameter slightly less than but close to the inside diameter of the catheter 12. It is probably preferred that the cutting cannula 22 is somewhat stiffer than the catheter 12. This does not mean that the cutting cannula 22 has to be stiff; to the contrary, while it is contemplated that the cutting cannula 22 can act as a stiffener for the catheter 12 during its introduction into the patient, it may still be desirable for the combination of the catheter 12 and the inserted cutting cannula 22 to have good flexibility to aid such introduction.

Unlike prior devices used for other purposes, it is the movement of the circumferential cutting edge 26 which primarily serves to cut and sever the material of interest. The lateral opening 20, 44 or 46 of the catheter 12 merely holds the tissue in place for cutting and aspiration by the cutting cannula 22. Moreover, unlike prior devices used for other purposes, the catheter 12 is by itself adapted to drain the abscess after the cutting cannula 22 has cut and aspirated the material of interest, and has been removed from the flow lumen 14 of the catheter 12.

Use of the medical device 10 according to the present invention for debriding an abscess in a patient, for removing debrided and other materials from the abscess and for draining the abscess can now be easily understood. If appropriate, the cutting cannula 22 is first introduced into the flow lumen 14 of the catheter 12 to act as a stiffener. The catheter 12 is then positioned in a suitable tear-away introducer sheath (not shown) if desired and introduced to the site of the abscess. Alternatively, the introducer sheath can be introduced by itself to a location near the site of the abscess, and the catheter 12 positioned in the sheath afterwards. Whether the cutting cannula 22 needs to be used as a stiffener, or whether a separate introducer sheath is required, depends upon the degree of flexibility needed to gain access to the abscess. Depending upon the site of the abscess, access may be had through an existing tract or passage in which the abscess has formed, or may be had through areas of tissue delamination caused by the abscess itself. In any case, the catheter 12 is introduced to a point where the lateral opening 20, 44 or 46 is positioned in the abscess in contact with any material to be debrided or removed. The cutting cannula 22 is introduced into the flow lumen 14, if not already positioned in it, and the suction source 32 is connected to the proximal end 30 of the cutting cannula 22 for aspirating the material to be debrided and removed. This causes material to be debrided to be drawn into engagement with the lateral opening 20, 44 or 46. The cutting cannula 22 is then reciprocated longitudinally in the flow lumen 14 so as to allow the circumferential cutting edge 26 to cut and sever the material to be debrided. The severed material is then aspirated through the cutting cannula 22 and out of the medical device 10. Once the abscess is debrided to the desired degree, the cutting cannula 22 is removed from the flow lumen 14, but the catheter 12 can be allowed to remain in place to permit continued drainage of the abscess for any desired length of time.

FIG. 8 is another preferred embodiment of the medical device 10 of the present invention including suction catheter 12 that is utilized without inner cutting cannula 22 received in lumen 14 of the suction catheter. In this particular embodiment, suction catheter 12 can be used for simple suction of fluid material such as aspirated material 54 being aspirated through lateral opening 20 of the suction catheter. Fluid material such as aspirated material 54 can be suctioned through lateral opening 20 when a source of suction (not shown) is connected to the proximal end of the device. The suction catheter of medical device 10 can also be used through an introducer sheath or cannula 50. Beveled distal end 52 of the introducer sheath or cannula 50 provides cutting capability of the aspirated material captured in the catheter's lateral opening 20, thereby shearing the tissue, clot or other material to be debrided.

FIG. 9 depicts a partially sectioned side view of yet another preferred embodiment of medical device 10 of the present invention. This embodiment is similar to the embodiment depicted in FIG. 1; however, suction catheter 12 further includes a second lumen 60 therein having a distal entry port into flow lumen 14 of the catheter. Second lumen 60 extends the length of the catheter in side portion or wall 18 of the catheter. This second lumen 60 and internal port 62 allows for the perfusion of saline to irrigate main flow lumen 14, thereby improving suction and reducing material buildup or clogging of the suction catheter. As previously discussed, cutting cannula 22 is disposed in main flow lumen 14 of the catheter for cutting or shearing debrided material, which is aspirated through lateral opening 20 of the catheter.

FIG. 10 depicts an enlarged cross-sectional side view of medical device 10 and in particular suction catheter 12 of FIG. 9 taken along the line 10—10. In this particular cross-sectional view, second lumen 60 is depicted in side portion or wall 18 of the catheter which runs in a generally longitudinal orientation with respect to main flow lumen 14.

It should be clear that the medical device 10 of the present invention is thus specifically structured not only to provide for the rapid debriding of an abscess in a human or veterinary patient, but also to permit the continued drainage of the abscess after debriding has been completed. The medical device 10 of the present invention thus possesses several significant advantages over prior devices not adapted to these specific uses. The medical device 10 of the present invention is capable of cutting blood clots and dead or necrotic tissues in or adjacent to the abscess and is capable of removing, by suction applied to the cutting cannula, any materials so cut. The catheter of the device is sufficiently flexible, however, to allow the device to be introduced into and through an tract in which an abscess has developed. The catheter of the device is also sufficiently flexible to further allow the device to be left in a patient for some time after the performance of a surgical technique, for draining the site at which the technique was performed. The abscess drainage device of the present invention is particularly adapted for all of these tasks, not just debriding as is the case with prior devices, and is structured to meet the particular problems encountered in debriding and draining an abscess. Finally, it is primarily the cutting cannula of the device which shears the tissue or other material to be debrided, in contrast to the more rigid prior devices in which the stiffness of an outer cannula contributes substantially to the shearing of such tissue or other material. The lateral opening in the catheter of the device instead merely holds tissues or other materials in place, while the cutting cannula cuts, severs and aspirates the tissues or other materials of interest.

The details of the construction or composition of the various elements of the medical device 10 of the present invention not otherwise disclosed are not believed to be critical to the achievement of the advantages of the present invention, so long as the elements possess the strength or flexibility needed for them to perform as disclosed. The selection of any such details of construction are believed to be well within the ability of one of even rudimentary skills in this area, in view of the present disclosure.

Industrial Applicability

The present invention is useful for debriding and draining an abscess, phlegmon, and hematoma which has developed in a human or veterinary patient, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A medical device particularly adapted for debriding an abscess, phlegmon, or hematoma in a human or veterinary patient, for removing debrided and other materials from the abscess and for draining the abscess, comprising:

a flexible catheter having a longitudinally extending flow lumen defined therein, a distal tip closing the flow lumen, a side portion extending proximally from the distal tip and a lateral opening formed in and extending through the side portion; and a cutting cannula positionable in and longitudinally slidable in the flow lumen in the catheter and being removable therefrom, having an open distal end and a circumferential cutting edge formed on the open distal end, the circumferential cutting edge moving across the lateral opening of the catheter upon longitudinal sliding movement of the cutting cannula in the flow lumen of the catheter and thereby cutting any material extending from the abscess and through the lateral opening of the catheter;

wherein the catheter is composed of at least one of a flexible medical grade material, vinyl, non-radiopaque vinyl, polyethylene, urethane, and a soft polymer material.

2. The device according to claim 1, wherein the catheter further has a proximal end opposite the distal tip, and wherein the device further comprises a side arm connected to the proximal end of the catheter in fluid communication with the flow lumen of the catheter.

3. The device according to claim 2, further comprising a fitting connecting the side arm to the proximal end of the catheter.

4. The device according to claim 1, wherein the circumferential cutting edge of the cutting cannula is sufficiently sharp to cut tissue at the treatment site with the cooperation of adjacent portions of the catheter without the catheter needing to be rigid.

5. The device according to claim 1, wherein the circumferential cutting edge of the cutting cannula is beveled.

6. The device according to claim 1, wherein the circumferential cutting edge of the cutting cannula is disposed perpendicularly to the flow lumen of the catheter.

7. The device according to claim 1, wherein the distal tip of the catheter is rounded.

8. The device according to claim 1, wherein the lateral opening of the catheter is oval in shape.

9. The device according to claim 1, wherein the cutting cannula further has a proximal end opposite the open distal end, and wherein the device further comprises a suction source connectable to the proximal end of the cutting cannula.

10. The device according to claim 1, wherein the catheter is adapted for introduction to the abscess and drainage of the abscess when the cutting cannula is not positioned in the flow lumen of the catheter.

11. The device according to claim 1, wherein the catheter is about 10–16 French (3–5 mm) in diameter.

12. The device according to claim 1, wherein the catheter is about 33 cm long.

13. The device according to claim 1, wherein the catheter further has a proximal end opposite the distal tip, and wherein the device further comprises a seal element located adjacent to the proximal end of the catheter through which the cutting cannula can be passed.

14. The device according to claim 1, wherein the cutting cannula is composed of at least one of a stainless steel, metal, tetrafluoroethylene, polyethylene terephthalate, and a medical grade material.

15. The device according to claim 1, wherein the lateral opening the catheter extends about one third of the way around the catheter.

16. The device according to claim 1, wherein the lateral opening of the catheter extends about 5 to 6 mm along the direction of the flow lumen.

17. A medical device particularly adapted for debriding an abscess, phlegmon, or hematoma in a human or veterinary patient, for removing debrided and other materials from the abscess and for draining the abscess, comprising:

a flexible catheter having a longitudinally extending flow lumen defined therein, a rounded distal tip closing the flow lumen, a side portion extending proximally from the distal tip and an oval lateral opening formed in and extending through the side portion, wherein the catheter is composed of at least one of a flexible medical grade material, vinyl, non-radiopaque vinyl, polyethylene, urethane, and a soft polymer material; and a cutting cannula positionable in and longitudinally slidable in the flow lumen in the catheter, and being removable therefrom, having an open distal end and a sharp, beveled circumferential cutting edge formed on the open distal end, the circumferential cutting edge being disposed perpendicularly to the flow lumen of the catheter and moving across the oval lateral opening of the catheter upon longitudinal sliding movement of the cutting cannula in the flow lumen of the catheter and thereby cutting any material extending from the abscess and through the lateral opening of the catheter;

wherein the cutting cannula further has a proximal end opposite the open distal end adapted for the application of suction thereto;

wherein the catheter is adapted for introduction to the abscess and drainage of the abscess when the cutting cannula is not positioned in the flow lumen of the catheter;

wherein the catheter is about 10–16 French (3–5 mm) in diameter and is about 33 cm long;

wherein the catheter further has a proximal end opposite the distal tip, and wherein the device further comprises a seal element located adjacent to the proximal end of the catheter through which the cutting cannula can be passed;

wherein the lateral opening of the catheter extends about one third of the way around the catheter and extends about 5 to 6 mm along the direction of the flow lumen; and wherein the device further comprises a side arm connected to the proximal end of the catheter in fluid communication with the flow lumen of the catheter and a fitting connecting the side arm to the proximal end of the catheter, the seal element being contained in the fitting.

18. A medical device particularly adapted for debriding an abscess in a human or veterinary patient, for removing debrided and other materials from the abscess and for draining the abscess, consisting of:

a flexible catheter having a longitudinally extending flow lumen defined therein, a rounded distal tip closing the flow lumen, a side portion extending proximally from the distal tip and an oval lateral opening formed in and extending through the side portion, wherein the catheter is composed of at least one of a flexible medical grade material, vinyl, non-radiopaque vinyl, polyethylene, urethane, and a soft polymer material; and a cutting cannula positionable in and longitudinally slidable in the flow lumen in the catheter, and being removable therefrom, having an open distal end and a sharp, beveled circumferential cutting edge formed on the open distal end, the circumferential cutting edge being disposed perpendicularly to the flow lumen of the catheter and moving across the oval lateral opening of the catheter upon longitudinal sliding movement of the cutting cannula in the flow lumen of the catheter and thereby cutting any material extending from the abscess and through the lateral opening of the catheter;

wherein the cutting cannula further has a proximal end opposite the open distal end adapted for the application of suction thereto;

wherein the catheter is adapted for introduction to the abscess and drainage of the abscess when the cutting cannula is not positioned in the flow lumen of the catheter;

wherein the catheter is about 12 French (4 mm) in diameter and is about 33 cm long;

wherein the catheter further has a proximal end opposite the distal tip, and wherein the device further consists of a seal element located adjacent to the proximal end of the catheter through which the cutting cannula can be passed;

wherein the lateral opening of the catheter extends about one third of the way around the catheter and extends about 5 to 6 mm along the direction of the flow lumen; and wherein the device further consists of a side arm connected to the proximal end of the catheter in fluid communication with the flow lumen of the catheter and a fitting connecting the side arm to the proximal end of the catheter, the seal element being contained in the fitting.

* * * * *